United States Patent [19]

Masukawa et al.

[11] Patent Number: 4,818,672
[45] Date of Patent: Apr. 4, 1989

[54] SILVER HALIDE COLOR PHOTOGRAPHIC LIGHT-SENSITIVE MATERIAL IMPROVED IN CYAN IMAGE CHARACTERISTICS

[75] Inventors: Toyoaki Masukawa; Yasuo Tsuda; Hidetaka Ninomiya; Noritaka Nakayama; Toshihiko Kimura, all of Hino, Japan

[73] Assignee: Konishiroku Photo Industry Co., Ltd., Tokyo, Japan

[21] Appl. No.: 60,058

[22] Filed: Jun. 9, 1987

[30] Foreign Application Priority Data

Jun. 13, 1986 [JP] Japan .................................. 61-138869
Oct. 31, 1986 [JP] Japan .................................. 61-261488

[51] Int. Cl.$^4$ ............................................... G03C 7/38
[52] U.S. Cl. ..................................... 430/558; 430/384; 430/385; 430/552
[58] Field of Search ................ 430/558, 384, 385, 552

[56] References Cited

U.S. PATENT DOCUMENTS 2,353,754  7/1944  Peterson ............................. 430/384
2,421,693  6/1947  Harriman ............................ 430/558
4,451,559  5/1984  Sato et al. .......................... 430/552
4,455,367  6/1984  Seoka et al. ........................ 430/552

FOREIGN PATENT DOCUMENTS 1545507  5/1979  United Kingdom .

Primary Examiner—Paul R. Michl
Assistant Examiner—Mark R. Buscher
Attorney, Agent, or Firm—Jordan B. Bierman

[57] ABSTRACT

A silver halide photographic light-sensitive material containing a novel cyan dye forming coupler is disclosed. The cyan dye forming coupler is represented by the following formula.

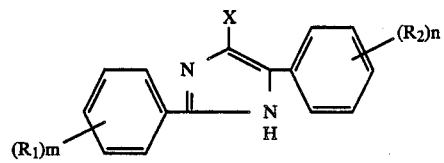

In the formula $R_1$ and $R_2$ are each a substituent, and X is a group capable of being splitted off from the coupler residue upon reaction of the coupler residue with the oxydized product of a color developing agent; and the total number of carbon atoms contained in the groups represented by $R_1$, $R_2$ and X is from 8 to 50. The spectral absorption characteristics of cyan dye images formed by the coupler of the invention are so sharp and steep that color reproduction can be achieved very advantageously.

3 Claims, 1 Drawing Sheet

SILVER HALIDE COLOR PHOTOGRAPHIC LIGHT-SENSITIVE MATERIAL IMPROVED IN CYAN IMAGE CHARACTERISTICS

FIELD OF THE INVENTION

This invention relates to a silver halide color photographic light-sensitive material containing a novel cyan dye forming coupler.

BACKGROUND OF THE INVENTION

A silver halide photographic light-sensitive material is exposed to light and is then color developed, during which a dye is produced upon reaction of an oxidized aromatic primary amine color developing agent with a dye forming coupler, so that a color image is formed.

Generally in the above-mentioned process, a color subtraction process is used for color reproduction so as to form color images in yellow, magenta and cyan, respectively.

As for such cyan color image forming couplers, phenols or napthols have popularly been used so far.

There is, however, a serious color reproduction problem in cyan images each formed with such phenols and naphthols having so far been used. The very problem is that there is an unnecessary spectral absorption. Namely, an unwanted irregular spectral absorption will take place in a green spectral region, because the spectral absorption is not sharp on the short wavelength side of a spectral transmission curve. Because of this problem, in negative light-sensitive materials, such an unwanted irregular spectral absorption has to be compensated by a masking or the like countermeasures, and in the case of print paper, there is not any countermeasure at all and color reproducibility is substantially deteriorated. Such as the state of things.

SUMMARY OF THE INVENTION

It is, accordingly, an object of the invention to provide a silver halide photographic light-sensitive material containing a novel cyan coupler capable of forming a cyan dye excellent in spectral absorption characteristics, namely, a sharp-cut spectral absorption on the short wavelength side and a substantially less irregular absorption in both green and blue spectral regions and also a substantially greater absorption coefficient.

The objects of the invention can be achieved with a silver halide color photographic light-sensitive material comprising a support having thereon at least one silver halide emulsion layer containing a cyan dye-forming coupler represented by the following formula [I]:

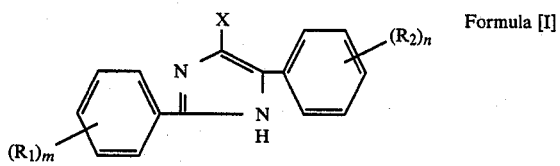

Formula [I]

wherein $R_1$ and $R_2$ represent each a group capable of being a substituent of a phenyl group and, m and n are each an integer of from 0 to 5; provided that both of m and n are not to be 0 at the same time and each of the groups represented by $R_1$ and $R_2$ may be the same with or the different from each other when a total of m and n is not less than 2 and the total number of carbon atoms contained in the groups represented by $R_1$ and $R_2$ is 8 to 50; and X represented a group or an atom capable of being splitted off from the coupler upon reaction of the coupler residue with the oxidized product of a color developing agent.

Figure 1:
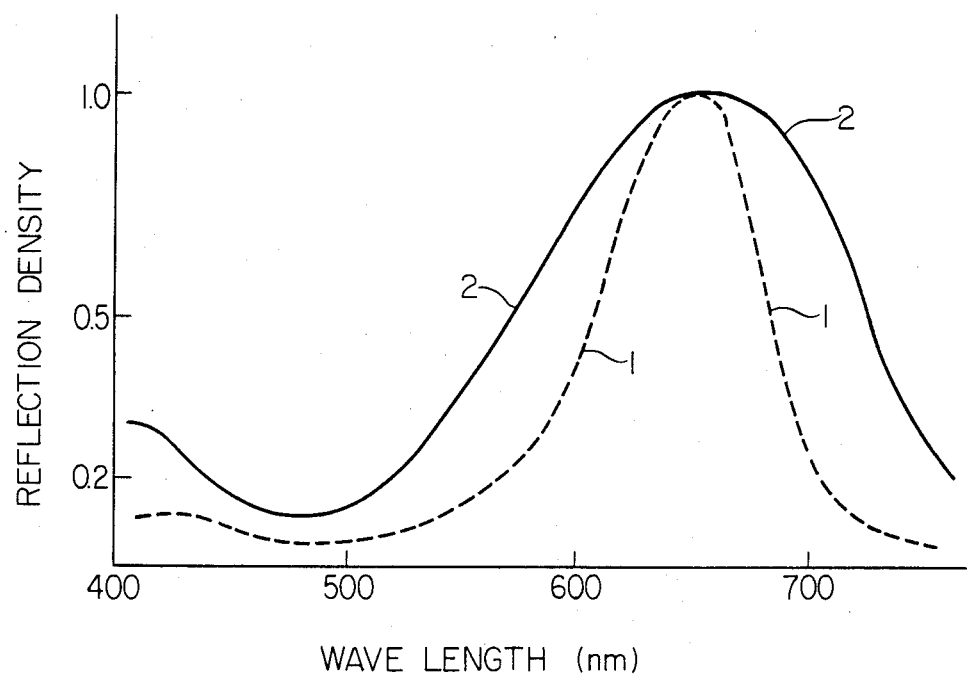
FIG. 1 is a graph exhibiting the spectral reflection densities of the cyan dye images respectively formed from Exemplified Couplers (2) of the invention represented by Formula [I] and from Comparative Coupler (A) each of which will be decribed later.

In the graph, Curves 1 and 2 show the results of the calculations using Exemplified Coupler (2) and Comparative Coupler (A), respectively.

DETAILED DESCRIPTION OF THE INVENTION

Now, the invention will be described in detail below.

The cyan couplers each represented by the above-given Formula [I] will first be described.

In Formula [I], the groups each represented by $R_1$ and $R_2$ substitutable to a phenyl group include, for example, a halogen atom, an alkyl group, an alkoxy group, a carbamoyl group, a sulfamoyl group, an alkoxycarbonyl group, a carboxy group, a cyano group, a nitro group, an —$NHCOR_3$ group, an

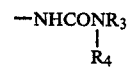

group, an —$NHCOOR_3$ group, an —$NHSO_2R_3$ group, an

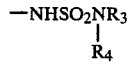

group, an —$NHR_3$ group or a hydroxy group, in which $R_3$ and $R_4$ represent each a hydrogen atom, an alkyl group or an aryl group.

It is important that the couplers of the invention is to be immobilized in such a degree that they may scarcely be eluted from a silver halide emulsion layer and it is, therefore, essential that the total number of carbon atoms contained in the groups represented by $R_1$, $R_2$ and X is 8 to 50.

It is also preferable that at least one of the groups represented by $R_1$ and $R_2$ is an —$NHCOR_3$,

—$NHCOOR_3$, —$NHSO_2R_3$,

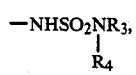

—$NHR_3$, or —OH group, in which $R_3$ and $R_4$ represent each a hydrogen atom, an alkyl group or an aryl group.

The groups, which are represented by X are capable of being splitted off upon reaction of the coupler residue with the oxidized product of a color developing agent, include, for example, a halogen atom, an —$OR_5$ group, an —$SR_5$ group, an

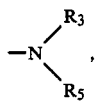

a heterocyclic group and so forth and, more preferably, a halogen atom and, more particularly, a chlorine atom, in which $R_5$ represents an alkyl, aryl or heterocyclic group.

The compounds each represented by the following Formula [II] may be given as the particularly preferable compounds among the compounds represented by the aforegiven Formula [I]:

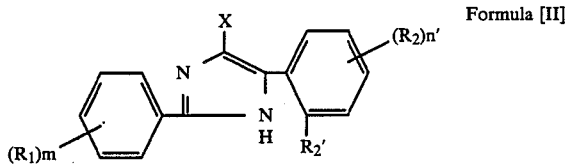

Formula [II]

wherein $R_1$, $R_2$, X and m are synonymous with those denoted in Formula [I]; n' is an integer of from 0 to 4; and $R'_2$ represents a group which is one of the groups represented by $R_2$ denoted in Formula [I], and has a hydrogen atom capable of forming a hydrogen bond with a nitrogen atom contained in the imidazole ring of Formula [II], (hereinafter called a hydrogen bond forming group); provided that the total number of the groups carbon atoms contained in the groups represented by $R_1$, $R_2$, $R'_2$ and X is 8 to 50.

The preferable examples of $R_2'$ include, typically, an —NHCOR$_3$ group, an

group, an —NHCOOR$_3$ group, an —NHSO$_2$R$_3$ group, an

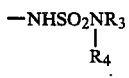

group, an —NHR$_3$ group and an —OH group, in which $R_3$ and $R_4$ represent each a hydrogen atom, an alkyl group or an aryl group.

A hydrogen-bond forming group represented by $R'_2$ is positioned at an ortho position of a phenyl group with respect to the coupling position of the phenyl group coupled to an imidazole ring, therefore, an excellent tone may be brought out for a cyan dye and an absorption coefficient may be sharply increased.

The above-mentioned alkylamido groups represented by —NHCOR$_3$ may typically be exemplified as the substituents to the groups each represented by $R_2'$ include non-substituted alkylamido groups each having 1 to 22 carbon atoms, such as an acetamido group, a butanamido group, a laurylamido group and a stearylamido group; and substituted alkylamido groups including halogen-substituted alkylamido groups such as a monochloracetamido, trifluoroacetamido, perfluorobutanamido and the like groups; phenoxy-substituted alkylamido groups such as m-pentadecylphenoxyacetamido, α-(2,4-di-t-amylphenoxy)pentanamido, α-(2,4-di-t-amylphenoxy)acetamido and so forth, and the like substituted alkylamido groups.

The typical examples of the above-mentioned arylamido groups represented by —NHCOR$_3$ may be given as follows. Non-substituted arylamido groups typically including a benzamido group, a naphthamido group and so forth; and substituted bezamido groups typically including alkyl-substituted benzamido groups such as a p-methylbenzamido group, a p-t-butylbenzamido group and so forth, alkoxy-substituted benzamido groups such as a p-methoxybenzamido group, an o-dodecyloxybenzamido group and so forth, amido-substituted benzamido groups such as a m-acetamidobenzamido group, a m-lauroylamidobenzamido group and so forth; and the like arylamido groups.

The typical examples of the above-mentioned alkylsulfonamido groups represented by —NHSO$_2$R$_3$ include non-substituted alkylsulfonamido groups having 1 to 22 carbon atoms, such as a methanesulfonamido group, an ethanesulfonamido group, a butanesulfonamido group and a dodecanesulfonamido group; and substituted alkylsulfonamido groups such as an aryl-substituted tuted alkylsulfonamido group, e.g., a benzylsulfonamido group and so forth.

The typical examples of the above-mentioned arylsulfonamido groups represented by —NHSO$_2$R$_3$ may given as follows:

Non-substituted arylsulfonamido groups such as a benzenesulfonamido group, a naphthalenesulfonamido group and so forth; and substituted arylsulfonamido groups including such an alkylbenzenesulfonamido group as a p-toluenesulfonamido group, a 2,4,6-trimethylbenzenesulfonamido group, a p-dodecylbenzenesulfonamido group and so forth, such an alkoxy-substituted benzenesulfonamido group as a p-dodecyloxybenzenesulfonamido group and so forth.

The typical examples of the above-mentioned dialkylcarbamoylamino groups represented by

include a dimethylcarbamoyl group, a diethylcarbamoyl group and so forth, and the typical examples of the above-mentioned dialkylsulfamoylamino groups include a dimethylsulfamoylamino group, a diethylsulfamoyl group and so forth.

In the above-given formula [I] or [II], the halogen atoms represented by $R_1$ and $R_2$ preferably include a chlorine atom and a bromine atom; the alkyl groups represented by $R_1$ and $R_2$ may be substituted and they include, for example, a methyl group, an ethyl group, a hydroxymethyl group, a hydroxyethyl group, a methoxyethyl group, a methanesulfonamidoethyl group and so forth; and the alkoxy groups represented by $R_1$ and $R_2$ may also be substituted and include, for example, a methoxy group, an ethoxy group, a dodecyloxy group, a pentadecyloxy group, a chlorobutoxy group and so forth.

The alkylamido, arylamido, alkylsulfonamido and arylsulfonamido groups each represented by $R_1$ and $R_2$ may be substituted, respectively, and they include the same groups as given in the same kinds of groups given for the groups together with the dialkylcarbamoylamino and dialkylsulfamoylamino groups, each represented by the aforedenoted A.

The group represented by X is the groups capable of being splitted off upon coupling reaction thereof with the oxidized products of an aromatic primary amine developing agent. They include, preferably, a halogen atom such as a chlorine atom, a bromine atom and so forth.

Next, the typical examples of the diphenylimidazole cyan couplers of the invention will be given below:

In the following table, position 6th corresponds to the position to which the group represented $R_2'$ is to be combined.

Formula [I]

[Structure: diphenylimidazole with substituents $(R_1)_m$ on one phenyl ring (positions 2,3,4,5,6 with 1 attached), central imidazole with N, NH, X groups, and $(R_2)_n$ on the other phenyl ring (positions 2,3,4,5,6 with 1 attached)]

| No. | X | $R_1$ | $R_2$ | m | n |
|---|---|---|---|---|---|
| 1 | H | — | $-NHCOC_{17}H_{35}$ (6th position) | 0 | 1 |
| 2 | —Cl | — | $-NHCOCHO-\underset{C_4H_9}{\phantom{X}}$—[phenyl with $C_5H_{11}(t)$ at 2-position, $C_5H_{11}(t)$ at 4-position] (6th position) | 0 | 1 |
| 3 | H | — | $-NHCOCHO-\underset{C_4H_9}{\phantom{X}}$—[phenyl with $C_5H_{11}(t)$ and $C_5H_{11}(t)$] (4th position) | 0 | 1 |
| 4 | H | — | $-NHCOCHO-\underset{C_2H_5}{\phantom{X}}$—[phenyl with $C_5H_{11}(t)$ and $C_5H_{11}(t)$] (3rd position) | 0 | 1 |
| 5 | H | —Cl (6th 4th position) | $-NHCOCH_2CH_2CH_2O-$[phenyl with $C_5H_{11}(t)$ and $C_5H_{11}(t)$] (6th position) | 2 | 1 |
| 6 | H | — | $-NHSO_2-$[phenyl]$-OC_{12}H_{25}$ (4th position) | 0 | 1 |
| 7 | H | $-OC_2H_5$ (4th position) | $-NHSO_2-$[phenyl with $OC_4H_9$ and $C_8H_{17}(t)$] (4th position) | 1 | 1 |
| 8 | H | $-CH_3$ (3rd position)<br>$-NHCOC_{12}H_{25}$ (4th position) | $-NHCONH-$[phenyl]$-CN$ (4th position) | 2 | 1 |

-continued

Formula [I]

[Structure: (R1)m-substituted phenyl (positions 2,3,4,5,6 around C1) connected via C=N to X, with adjacent C having NH and bonded to (R2)n-substituted phenyl (positions 2,3,4,5,6 around C1)]

| No. | X | $R_1$ | $R_2$ | m | n |
|-----|---|-------|-------|---|---|
| 9 | H | — | -NHCOCH$_2$CH$_2$-[3,5-di-$C_4H_9(t)$-4-OH-phenyl] (4th position) | 0 | 1 |
| 10 | H | — | -CH$_3$ (6th position); -NHSO$_2$-[2-$OC_8H_{17}$-3,5-di-$C_5H_{11}(t)$-phenyl] (4th position) | 0 | 2 |
| 11 | H | -NHCOCHO-[2,4-di-$C_5H_{11}(t)$-phenyl] (3rd position) | — | 1 | 0 |
| 12 | H | — | -NHCOC(CH$_3$)$_2$CH$_2$SO$_2$-[4-NHCOCH$_3$-phenyl] (3rd position) | 0 | 1 |
| 13 | H | -OC$_{12}$H$_{25}$ (4th position) | -NHCOCCl$_3$ (4th position) | 1 | 1 |
| 14 | H | -CN (4th position) | -NHSO$_2$C$_8$H$_{17}$ (6th position) | 1 | 1 |
| 15 | -Cl | -NO$_2$ (3rd position) | -NHCOCH(C$_4$H$_9$)O-[2,4-di-$C_5H_{11}(t)$-phenyl] (6th position) | 1 | 1 |
| 16 | H | -Cl (4th position) | -NHCOCH(C$_4$H$_9$)O-[2,4-di-$C_5H_{11}(t)$-phenyl] (6th position) | 1 | 1 |
| 17 | -Cl | — | -NHCOCH(C$_4$H$_9$)O-[2,4-di-$C_5H_{11}(t)$-phenyl] (4th position) | 0 | 1 |
| 18 | -Cl | — | -NHCOCH(C$_4$H$_9$)O-[2,4-di-$C_5H_{11}(t)$-phenyl] (3rd position) | 0 | 1 |

-continued

Formula [I]

[Structure: bis-aryl compound with formula showing two phenyl rings connected through N=C(X)–CH=C(NH–)– linkage, with $(R_1)_m$ on left ring and $(R_2)_n$ on right ring]

| No. | X | R₁ | R₂ | m | n |
|---|---|---|---|---|---|
| 19 | H | —COOC₂H₅ (4th position) | —NHCOCH₂O—[2,4-di-$C_5H_{11}(t)$-phenyl] (6th position) | 1 | 1 |
| 20 | H | —CONH₂ (4th position) | —NHCOCH(C₄H₉)O—[2,4-di-$C_5H_{11}(t)$-phenyl] (6th position) | 1 | 1 |
| 21 | H | —NHCOCH(C₄H₉)O—[2,4-di-$C_5H_{11}(t)$-phenyl] (4th position) | —NHCOCH₃ (6th position) | 1 | 1 |
| 22 | —Cl | —CONHCH₂CH₂CH₂CH₂O—[2,4-di-$C_5H_{11}(t)$-phenyl] (4th position) | —NHCOCH₃ (6th position) | 1 | 1 |
| 23 | —Cl | —NHSO₂—[2-$OC_8H_{17}$, 5-$C_8H_{17}(t)$-phenyl] (6th position) | —F (6th 4th position) | 1 | 2 |
| 24 | —Cl | —NHCOCH₃ (4th position) | —SO₂NHCH₂CH₂CH₂CH₂O—[2,4-di-$C_5H_{11}(t)$-phenyl] (4th position) | 1 | 1 |
| 25 | —Cl | —COOH (4th position) | —NHSO₂—[2-$OC_8H_{17}$, 5-$C_8H_{17}(t)$-phenyl] (3rd position) | 1 | 1 |

-continued

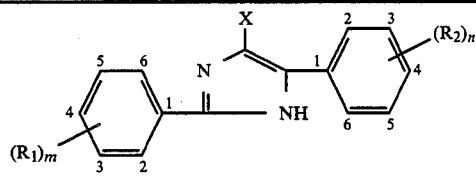

Formula [I]

| No. | X | R₁ | R₂ | m | n |
|---|---|---|---|---|---|
| 26 | H | ![structure: 4-OC₈H₁₇ phenyl with NHSO₂ linked to another phenyl bearing OC₈H₁₇ and C₈H₁₇(t), NHSO₂ at 3-position] (4th position) | | 1 | 0 |
| 27 | H | — | —NHCOOCH₂CH(Et)(CH₂)₃CH₃ (6th position) | 0 | 1 |
| 28 | H | —NHCOOCH₂CH(CH₃)₂ (4th position) | —NHCOCH(C₄H₉)O—[2,4-di-C₅H₁₁(t)phenyl] (6th position) | 1 | 1 |
| 29 | H | —NHCOCH(C₂H₅)O—[2,4-di-C₅H₁₁(t)phenyl] (4th position) | —CONHCOCH(C₂H₅)O—[2,4-di-C₅H₁₁(t)phenyl] (6th position) | 1 | 1 |
| 30 | —Cl | —NHCOC₁₁H₂₃ (4th position) | —NHCO—(pentafluorophenyl) (6th position) | 1 | 1 |
| 31 | H | — | —SO₂NH(CH₂)₃OC₁₂H₂₅ (4th position) | 0 | 1 |
| 32 | H | — | —OC₁₆H₃₂ (6th position) | 0 | 1 |
| 33 | H | —NHCOCH₂C(CH₃)₃ (4th position) | —NHSO₂N(CH₃)₂ (6th position) | 1 | 1 |
| 34 | H | —NHCOCH(C₂H₅)C₄H₉ (4th position) | —NH₂ (2nd position) | 1 | 1 |
| 35 | H | —OH (4th position) | —NHCO—[2-(NHCOCH₂C(CH₃)₃)phenyl] (6th position) | 1 | 1 |

The diphenylimidazole cyan couplers of the invention may be synthesized in accordance with the process, for example, reported by Franz Kunkell in Chemische Berichte, vol. 34, p. 639, for example. A typical synthesis example will be given below.

SYNTHESIS EXAMPLE-1

Synthesis of 2-phenyl-4-(o-stearylamidophenyl)imidazole

Compound Example (1)

Benzamidine hydrochloride of 4.0 g was dissolved in 20 ml of water. The resulted solution was added with a solution of 3.3 g of caustic potash dissolved in 7.5 ml of water and then with 15 ml of chloroform. The whole amount of the resulted solution was poured into a separating funnel and was then shaked well so as to extract free benzamine in a chloroform layer.

After the chloroform layer was separated therefrom, 3.0 g of o-stearylamido-α-bromoacetophenone was added into the separated chloroform. After the resulted solution was boiled and refluxed for 2 hours and was then cooled, the chloroform was distilled off under reduced pressure. The residue was washed several times with water and was then crystallized by adding 100 ml of methanol. The filtrated crystals were recrystallized with an ethyl acetate-methanol mixed solution.

Yield: 1.52 g. Melting point: 169° to 174° C.

SYNTHESIS EXAMPLE-2

Synthesis of 2-phenyl-4-[o-[α-(2,4-di-t-amylphenoxyhexanamido]-phenyl-5-chlorimidazole

Compound example (2)

The dissolution of 10 g (17.7 mmol) of the above-given compound of Compound Example (6), i.e., 2-phenyl-4-[o-{α-(2,4-di-t-amylphenoxyhexanamido} phenylimidazole, were made in 150 ml of chloroform, and 2.9 g (19.3 mmol) of a (90%) NCS were added thereto at room temperature and while stirring. After one hour, 2.9 g of NCS were further added. The resulted solution was allowed to stand overnight and were then washed, distilled to take out the solvents and dissolved in 100 ml of acetonitrile so as to be recrystallized, and the recrystallized matter was washed. Thereby, 5.7 g of Compound Example (7) were obtained in the form of light-green crystals.

Yield: 53.7% Melting point: 155° to 158° C.

SYNTHESIS EXAMPLE-3

Synthesis of 2-phenyl-4-[p-{α-(2,4-di-t-amylphenoxy)hexanamido} phenyl]imidazole

Compound Example (3)

p-{α-(2,4-di-t-amylphenoxy)hexanamido}-α-bromacetophene of 5.44 g were dissolved in 30 ml of chloroform and 40 ml of a free-state 0.1 mol benzamidine-chloroform solution were dropped into the resulted solution at room temperature. After the resulted solution was stirred for one hour, the chloroform was distilled off from the solution under reduced pressure. The resulted matter was dissolved in 200 ml of ethanol and was then washed with 50 ml of an aqueous 5% $K_2CO_3$ solution and further with 50 ml of water. The resulted matter was dried and $MgSO_4$ and ethanol was distilled off therefrom. A fractionation was made with a silica gel column using ethanol and hexane=1:1 and the solvent was distilled off, so that 4.2 g of a solid was obtained.

Yield: 74%.

SYNTHESIS EXAMPLE-4

Synthesis of 2-phenyl-4-[p-{α-(2,4-di-t-amylphenoxy)hexanamido} phenyl]-5-chloroimidazole

Compound Example (17)

The solid prepared in Synthesis Example-2 of 1.13 g in 2 millimol were dissolved in 10 ml of chloroform and 0.3 g of N-chlorosuccinimide (NCS) were added thereto. The resulted solution was stirred at room temperature for two days and were then washed. When the solvent was distilled off, a thick syrup-like matter was obtained. The crystallization thereof was tried with 10 ml of methanol, so that 0.71 g of light-green crystals were obtained.

Yield: 59%, Melting point: 109° to 112° C.

SYNTHESIS EXAMPLE-5

Synthesis of 2-phenyl-4-[{-p-(p-dodecyloxybenzene)sulfonamido} phenyl]imidazole

Synthesis of Compound Example (6)

A synthesis was made in the same manner as in the above-mentioned syntheses Example-3, except that 5.44 g of p-{α-(2,4-di-t-amylphenoxy)hexanamido}-α-bromacetophenone were replaced by 5.38 g of p-(p-dodecyloxybenzene)sulfonamido-α-bromacetophenone and 3.5 g of a white solid were obtained.

Yield: 62%.

SYNTHESIS EXAMPLE-6

Synthesis of 2-p-chlorophenyl-4-[o-{α-(2,4-di-t-amylphenoxy)hexanamido}phenyl]imidazole

Synthesis of Compound Example (16)

Chloroform of 20 ml and DMF of 15 ml were added into 11.3 g of p-chlorobenzamidine hydroiodide and an aqueous solution prepared by adding 2.24 g of KOH into 10 ml of water was further added thereto. The resulted solution was stirred at room temperature for 10 minutes. After stirring, the solution prepared by dissolving 5.44 g of o-{α-(2,4-di-t-amylphenoxyhexanamido}-α-bromaetophenone in 20 ml of $CHCl_3$ was dropped into the above-mentioned solution by taking 10 minutes.

When the solution was allowed to stand after beating up for three hours, the solution was separated into two strata. After removing the aqueous stratum, the remaining stratum was washed in 20 ml of water and the solvents were distilled off under reduced pressure. When the residue was crystallized with acetonitrile, 1.45 g of crystals were obtained.

Yield: 24%, Melting point 135° to 139° C.

The couplers of the invention are added into a silver halide emulsion layer, in an amount of, preferably, from 0.07 mol to 0.7 mol and, more preferably, from 0.1 mol to 0.4 mol per mol of silver contained in the silver halide emulsion layer.

Any silver halide emulsion layers containing the couplers of the invention each represented by the aforegiven formula [I] and any light-sensitive materials of the invention are allowed to contain not only the couplers represented by the aforegiven formula [I] but other couplers including a colorless coupler capable of producing a colorless compound upon coupling reaction thereof with the oxidized products of a color developing agent, and a DIR compound capable of producing a colorless compound and, simultaneously, releasing a development inhibitor upon the similar coupling reaction.

Such couplers as given above will now be described.

The couplers which may be used in combination include, preferably, non-diffusible couplers each having the so-called ballast groups, i.e., hydrophobic groups. Such couplers may be either any one of the so-called 4-equivalent couplers each require 4 mol of silver to produce 1 mol of a color-forming dye, or any one of 2-equivalent couplers each require 2 mol of silver to produce the same. They may further be DIR couplers each capable of releasing a development inhibitor, colored couplers each capable of displaying a color compensation effect, and so forth.

The yellow color forming couplers include publicly-known open-chained ketomethylene type couplers, namely, benzoylacetanilide type couplers, pivaloylacetanilide type couplers, and so forth. The typical examples thereof include those described in British Pat. No. 1,077,874; Japanese Patent Examined Publication No. 40757/1970; Japanese Patent O.P.I. Publication Nos. 1031/1972, 26133/1972, 94432/1973, 87650/1975, 3631/1976, 115219/1977, 99433/1979, 133329/1979 and 30127/1981; U.S. Pat. Nos. 2,875,057, 3,253,924, 3,265,506, 3,408,194, 3,551,155, 3,551,156, 3,664,841, 3,725,072, 3,730,722, 3,891,445, 3,900,483, 3,929,484, 3,933,500, 3,973,968, 4,012,259, 4,022,620, 4,029,508, 4,057,432, 4,106,942, 4,133,958, 4,269,936, 4,286,053, 4,304,845, 4,314,023, 4,336,327, 4,356,258, 4,386,155 and 4,401,752; and so forth.

The magenta dye forming couplers which may preferably be used include, for example, a 5-pyrazolone type coupler, a pyrazolobenzimidazole type coupler, a pyrazolotriazole type coupler and an open-chained acylacetonitrile type coupler.

The typical examples of advatageously useful magenta couplers include those described in Japanese Patent Applications Nos. 164882/1983, 167326/1983, 206321/1983, 214863/1983 217339/1983 and 24653/1984; Japanese Patent Examined Publication Nos. 6031/1965, 6035/1965, 40757/1970, 27411/1972 and 37854/1974; Japanese Patent O.P.I. Publication Nos. 13041/1975, 26541/1976, 37646/1976, 105820/1976, 42121/1077, 123129/1078, 125835/1978, 129035/1978, 48540/1979, 29236/- 1981, 75648/1981, 17950/1982, 35858/1982, 146251/1982 and 99438/1984; British Pat. No. 1,252,418; U.S. Pat. Nos. 2,600,788, 3,005,712, 3,062,653, 3,127,269, 3,214,437, 3,253,924, 3,311,476, 3,419,391, 3,519,429, 3,558,319, 3,582,322, 3,615,506, 3,658,544, 3,705,896, 3,725,067, 3,758,309, 3,823,156, 3,834,908, 3,891,445, 3,907,571, 3,926,631, 3,928,044, 3,935,015, 3,960,571, 4,076,533, 4,133,686, 4,237,217, 4,241,168, 4,264,723, 4,301,235 and 4,310,623; and so forth.

The preferably useful cyan dye forming couplers include, for example, the well-known naphthol type and phenol type couplers. The typical examples of the advantageously useful cyan couplers are those described in British Pat. Nos. 1,038,331 and 1,543,040; Japanese Patent Examined Publication No. 36894/1973; Japanese Patent O.P.I. Publication Nos. 59838/1973, 137137/1975, 146828/1976, 105226/1978, 115230/1979, 29235/1981, 104333/1981, 126833/1981, 133650/1982, 155538/1982, 204545/1982, 118643/1983, 31953/1984, 31954/1984, 59656/1984, 124341/1984 and 166956/1984; U.S. Pat. Nos. 2,369,929, 2,423,730, 2,434,272, 2,474,293, 2,698,794, 2,772,162, 2,801,171, 2,895,826, 3,253,924, 3,311,476, 3,458,315, 3,476,563, 3,591,383, 3,373,316, 3,758,308, 3,767,411, 3,790,384, 3,880,661, 2,926,634, 4,004,929, 4,009,035, 4,012,258, 4,052,212, 4,124,396, 4,134,766, 4,138,258, 4,146,396, 4,149,886, 4,178,183, 4,205,990, 4,254,212, 4,264,722, 4,288,532, 4,296,199, 4,296,200, 4,299,914, 4,333,999, 4,334,011, 4,386,155, 4,401,752 and 4,427,767; and so forth.

The colored couplers which may be used include, for example, those described in U.S. Pat. Nos. 2,449,966, 3,476,560, 2,521,908, 2,543,691, 2,801,171, 3,208,238, 3,034,892, 3,061,432, 3,476,563 and 3,519,429; Japanese Patent Examined Publication Nos. 22335/1963, 11034/1967, 2016/1969, 32461/1969 and 27930/1973; Japanese Patent O.P.I. Publication Nos. 26034/1976 and 42121/1977; West German Patent (OLS) No. 2,418,959; British Pat. No. 1,035,959; and so forth.

The DIR couplers include, for example, the compounds described in British Pat. No. 953,454; U.S. Pat. Nos. 3,227,554, 3,615,506, 3,617,291, 3,701,783, 3,933,500, 4,095,984, 4,149,886, 4,286,054 and 4,359,521; Japanese Patent O.P.I. Publication Nos. 90932/1977, 116029/1981, 151944/1982 and so forth; and the timing DIR couplers described in U.S. Pat. Nos. 4,248,962 and 4,409,323; Japanese Patent O.P.I. Publication Nos. 154234/1982, 162949/1983, 205150/1983, 195643/1984, 206834/1984, 206836/1984, 210440/1984 and 7429/1985; and so forth.

The preferably useful DIR compounds include, for example, the compounds described in U.S. Pat. Nos. 3,632,345, 3,928,041, 3,938,996, 3,958,993, 3,961,959, 4,046,574, 4,052,213, 4,171,223 and 4,186,012; Japanese Patent O.P.I. Publication Nos. 65433/1977, 130327/1977, 128335/1982; and so forth.

As for the non-dye-forming couplers, the so-called Weiss coupler described in U.S. Pat. Nos. 2,998,314 and 1,284,649; and West German Patent No. 1,168,769 may be used for adjusting tones and preventing color-contamination and fog.

It is also allowed to add two or more kinds of the above-mentioned couplers into one and the same layer and, further, to add one and the same compound into two or more layers different from each other.

The above-mentioned couplers are to be added, in an emulsion layer, generally in an amount of from $2 \times 10^{-3}$ mol to $5 \times 10^{-1}$ mol and, more preferably, from $1 \times 10^{-2}$ mol to $5 \times 10^{-1}$ mol per mol of silver contained in the emulsion layer.

In order to introduce the above-mentioned couplers into a silver halide emulsion, any well-known methods such as the method described in U.S. Pat. No. 2,322,027 and the like methods may be used.

Out of a dye-forming coupler, a colored coupler, a DIR coupler, a DIR compound, an image stabilizer, a color-fog preventing agent, a UV absorbing agent, an optical brightening agent and so forth, each of which is not necessary to adsorb to the surfaces of silver halide crystals, hydrophobic compounds may be treat in a variety of processes, such as a solid dispersion process, a latex dispersion process, an oil-drop-in-water type emulsification-dispersion process and so forth. These processes may be appropriately selected to use in accordance with the chemical structures and so forth of such hydrophobic compounds as couplers and so forth. Any conventionally well-known oil-drop-in-water type dispersion processes may be so applied as to disperse hydrophobic compounds such as couplers and so forth. Normally, in the processes, a hydrophobic compound is dissolved in a high boiling organic solvent having a boiling point of not lower than about 150° C. and if required in combination with a low boiling and/or water-soluble organic solvent, and the resulting solution is emulsified and dispersed in hydrophilic binders such as an aqueous gelatin solution with a surface active agent by making use of a dispersing means such as a stirrer, a homogenizer, a colloid mill, a flow-jet mixer, a ultrasonic homogenizer and so forth and, after then, the resulting emulsification-dispersion may be added into an objective hydrophilic colloidal layer.

It is allowed to carry out a step of removing the low boiling organic solvent either after dispersion or at the same time of dispersion.

In the invention, a proportion of a high boiling organic solvent to a low boiling organic solvent is preferably from 1:0.1 to 1:50 and more preferably from 1:1 to 1:20.

As for the high boiling solvents, organic solvents each having a boiling point of not lower than 150° C. may be used, such as a phenol derivative, an alkyl phthalate, a phosphate, a citrate, a benzoate, an alkylamide, a fatty acid ester, a trimesic acid ester and so forth, each of which is incapable of reacting with the oxidized products of a developing agent.

The high boiling organic solvents capable of being used in the invention include, for example, those described in U.S. Pat. Nos. 2,322,027, 2,533,514, 2,835,579, 3,287,134, 2,353,262, 2,852,383, 3,554,755, 3,676,137, 3,676,142, 3,700,454, 3,748,141, 3,779,765 and 3,837,863; British Pat. Nos. 958,441 and 1,222,753; West German OLS Patent No. 2,538,889; Japanese Patent O.P.I. Publication Nos. 1031/1972, 90523/1974, 23823/1975, 26037/1976, 27921/1976, 27922/1976, 26035/1976, 26036/1976, 62632/1975, 1520/1978, 1521/1978, 15127/1978, 119921/1979, 119922/1979, 25057/1980, 36869/1980, 19049/1981 and 81836/1981; Japanese Patent Examined Publication No. 29060/1973; and so forth.

The low boiling or water-soluble organic solvents capable of being used together with or in place of the above-mentioned high boiling solvents include, for example, those described in U.S. Pat. No. 2,801,171 and 2,949,360; and so forth. The low boiling and substantially water-insoluble organic solvents include, for example, ethyl acetate, propyl acetate, butyl acetate, butanol, chloroform, carbon tetra-chloride, nitromethane, nitroethane, benzene and so forth. And, the water-soluble organic solvents include, for example, acetone, methylisobutyl ketone, $\beta$-ethoxyethyl acetate, methoxyglycol acetate, methanol, ethanol, acetonitrile, dioxane, dimethylformamide, dimethylsulfoxide, hexamethylphosphoramide, diethyleneglycolmonophenyl ether, phenoxyethanol and so forth.

The latex dispersion processes include, preferably, those described in U.S. Pat. Nos. 4,199,363, 4,214,047, 4,203,716 and 4,247,627; Japanese Patent O.P.I. Publication Nos. 74538/1974, 59942/1976, 59943/1976 and 32552/1979; and so forth.

The surface active agents for serving as a dispersion assistant preferably include, for example, such an anionic surface active agent as an alkylbenzene sulfonate, an alkylnaphthalene sulfonate, an alkyl sulfonate, an alkyl sulfate, an alkyl phosphate, a sulfosuccinate, a sulfoalkylpolyoxyethylenealkylphenyl ether and so forth; such a nonionic surface active agent as a steroid type saponin, an alkylene oxide derivative, a glycidol and so forth; such an amphoteric surface active agent as an amino acid salt, an aminoalkylsulfonic acid, an alkylbetaine and so forth; and such a cationic surface active agent as a quaternary ammonium salt and so forth. The typical examples of these surface active agents are described in, for example, 'A Handbook of Surface Active Agents', published by Sangyo Tosho Publishing Co., 1966, and 'A Research on Emulsifiers and Emulsifying Apparatuses, and the Technical Data thereof', published by Kagaku Hanron Sha Publishing Co., 1978.

A color-fog preventing agent may be so used as to prevent color contamination, a sharpness deterioration and a coarse graininess produced by the migration of the oxidized products of a developing agent or of an electron-transferring agent between the emulsion layers (i.e., between the same and/or different color-sensitive layers) of the light-sensitive materials of the invention.

Such a color-fog preventing agent may be added either in emulsion layers in themselves or in an interlayer interposed between the emulsion layers adjacent to the emulsion layers.

Such color-fog preventing agents preferably include, for example, a hydroquinone derivative, an aminophenol derivative, a gallic acid derivative, an ascorbic acid derivative and so forth. The typical examples thereof are described in, for example, U.S. Pat. Nos. 2,360,290, 2,336,327, 2,403,721, 2,418,613, 2,675,314, 2,701,197, 2,704,713, 2,728,659, 2,732,300, 2,735,765 and 3,700,453; Japanese Patent O.P.I. Publication Nos. 92988/1975, 92989/1975, 93928/1975, 110337/1975, 156438/1975, 146235/1977, 95948/1980 and 5247/1984; Japanese Patent Examined Publication No. 23813/1975; and so forth.

In the light-sensitive materials of the invention, an image stabilizer may be so used as to prevent dye images from deterioration.

Such image stabilizers preferably include, for example, a hydroquinone derivative, a gallic acid derivative, a phenol derivative and the bis substances thereof, a hydroxycoumarin and the spiro substances thereof, a hydroxychroman and the spiro substances thereof, a piperidine derivative, an aromatic amine compound, a benzodioxane derivative, a benzdioxol derivative, a silicon atom-containing compound, a thioether compound and so forth. The typical examples thereof include those described in, for example, British Pat. No. 1,410,846; Japanese Patent O.P.I. Publication Nos. 134326/1974, 35633/1977, 147434/1977, 150630/1977, 145530/1979, 6321/1980, 21004/1980, 124141/1980, 3432/1984, 5246/1984 and 10539/1984; Japanese Patent Examined Publication Nos. 31625/1973, 20973/1974, 20974/1974, 23813/1975 and 27534/1977; U.S. Pat. Nos. 2,360,290, 2,418,613, 2,675,314, 2,701,197, 2,704,713, 2,710,801, 2,728,659, 2,732,300, 2,735,765, 2,816,028, 3,069,262, 3,336,135, 3,432,300, 3,457,079, 3,573,050, 3,574,627, 3,698,909, 3,700,455, 3,764,337, 3,935,016, 3,982,944, 4,013,701, 4,113,495, 4,120,723, 4,155,765, 4,159,910, 4,254,216, 4,268,593, 4,279,990, 4,332,886, 4,360,589, 4,430,425 and 4,452,884; and so forth.

Hydrophilic colloidal layers such as protective layers, interlayers and so forth each used in the light-sensitive materials of the invention may also contain a UV absorbing agent with the purposes of preventing fogs produced by a discharge from a frictional charge or the like generated in the light-sensitive materials and also preventing an image deterioration caused by ultraviolet rays.

The UV absorbing agents used therein include, for example, benzophenone compounds such as those described in Japanese Patent O.P.I. Publication No. 2784/1971; butadiene compounds such as those described in U.S. Pat. No. 4,045,229; 4-thiazolidone compounds such as those described in U.S. Pat. Nos. 3,314,794 and 3,352,681; benzothriazole compounds substituted with an aryl group such as those described in U.S. Pat. Nos. 3,533,794 and 4,323,633; benzoxazole compounds such as those described in U.S. Pat. No. 3,700,455; and cinnamate compounds such as those described in U.S. Pat. Nos. 3,705,805 and 3,707,375. Besides, those described in U.S. Pat. No. 3,499,762 and Japanese Patent O.P.I. Publication No. 48535/1979 may also be used. Further, UV-absorbable couplers such as α-naphthol type cyan dye forming couplers, UV-absorbable polymers such as those described in Japanese Patent O.P.I. Publication Nos. 111942/1983 and 178351/1983 and so forth may also be used. These UV absorbing agents may be mordanted in a specific layer.

A formalin scavenger may also be used in the light-sensitive materials of the invention so as to prevent any deterioration of magenta dye forming couplers and so forth caused by formalin during the storage of the light-sensitive materials.

The formalin scavengers preferably used therein include, for example, those described in Japanese Patent O.P.I. Publication Nos. 87028/1975, 133450/1982 and 150950/1983; U.S. Pat. Nos. 2,895,827, 3,652,278, 3,811,891, 4,003,748, 4,411,987, 4,418,142 and 4,464,463; U.S. Patent Defensive Publication No. 900,028; West German Patent Nos. 3,223,699, 3,227,961 and 3,227,962; Research Disclosure, No. 10133; and so forth.

The silver halide emulsion layers and/or the other hydrophilic colloidal layers of the light-sensitive materials of the invention are also allowed to contain the compounds each capable of adjusting the developability the light-sensitive materials, such as a development accelerator, a development inhibitor and so on, as well as a bleach accelerator.

The compounds each preferably used therein for such a development accelerator as mentioned above include, for example, those described in Research Disclosure No. 17463, Article XXI, Items B through D. The development inhibitors include, for example, the compounds each given in Research Disclose, No. 17463, Article XXI, Item E. Besides the above, black-and-white developing agents and/or the precursors thereof may also be used with the purpose of accelerating developments or with the other purposes.

The photographic emulsion layers of the light-sensitive materials of the invention are also allowed to contain a polyalkylene oxide or the derivatives thereof such as those of ether, ester, amine and so forth, a thioether compound, a thiomorpholine, a quaternary ammonium compound, a urethane derivative, a urea derivative, an imidazole derivative and so on, for the purposes of increasing sensitivity and contrast or improving developability.

An optical brightening agent may also be added to the light-sensitive materials of the invention, with the purposes of emphasizing whiteness and making any coloration unobtrusive in white areas.

Such optical brightening agents preferably used therein include, for example, those of stilbene type, triazine type, imidazolone type, pyrazoline type, triazole type, coumaran type, acetylene type, oxazole type and oxadiazole type. These optical brightening agents are described in, for example, U.S. Pat. Nos. 2,571,706, 2,581,057, 2,618,636, 2,702,296, 2,713,054, 2,715,630, 2,723,193, 3,513,102, 3,684,729, 3,788,854 and 3,789,012; British Pat. Nos. 669,590, 672,803 and 712,764; Netherlandish Patent No. 74,109; West German Pat. No. 911,368; West German (OLS) Pat. No. 2,525,680; and so forth. These compounds may be either water-soluble or insoluble, provided those in the latter case are to be in the form of a dispersion.

The light-sensitive materials of the invention may be provided with such an auxiliary layers as a filter layer, an antihalation layer and/or an antiirradiation layer and so forth. These layers and/or the emulsion layers thereof may also contain such a dyestuff capable of eluting or being bleached off therefrom in the course of developing the light-sensitive materials.

In the light-sensitive materials of the invention, the silver halide emulsion layers each containing the silver halide emulsions of the invention and/or the other hydrophilic colloidal layers are allowed to contain a matting agent for the purposes of reducing the gross, improving retouching property, preventing the adhesion to each other light-sensitive materials and so forth.

The light-sensitive materials each containing the silver halide emulsions of the invention are also allowed to contain an antistatic agent with the purpose of preventing electrostaticity. Such antistatic agents may be applied to an anti-static layer arranged to the support surface not coated with any emulsion, and to emulsion layers and/or other protective colloidal layer provided to the emulsion layer coated side of the support. The antistatic agents preferably used therein include, for example, the compounds described in Research Disclosure No. 17643, XIII.

A variety of surface active agents may be added in the photographic emulsion layers and/or the other hydrophilic colloidal layers of the light-sensitive materials of the invention, for the purposes of improving coatability, anti-static property, slipping property, emulsification-dispersion property, adhersion prevention property, photographic characteristics such as development acceleration property, hardening property, sensitization property and the like.

The supports each used in the light-sensitive materials of the invention include, for example, a flexible reflection type support made of, for example, a sheet of paper laminated with an α-olefin polymer such as polyethylene, polypropylene or ethylene/butene copolymer and so forth; a flexible support made of a film sheet comprising a semisynthetic or synthetic cellulose acetate, cellulose nitrate, polystyrene, polyvinyl chloride, polyethylene terephthalate, polycarbonate, polyamide and so forth, or those made of such a film provided thereon with a reflection layer; and a glass plate, a metal plate, an earthware plate; and so forth.

In the light-sensitive materials of the invention, the surface of the support thereof is applied, if required, with a corona-discharge, ultraviolet irradiation, flame treatment or the like treatments, and is then coated with a photographic layer thereon, directly or through one or more subbing layers which are to improve the adhesion property of the surface of the support, an antistatic property, a dimensional stability, an antiabrasion property, a hardness, an antihalation property, an antifriction property and/or the other properties.

In the silver halide emulsions used in the light-sensitive materials of the invention, any of silver halides being used in the popular silver halide emulsions may be used, such as silver bromide, silver iodobromide, silver iodochloride, silver chlorobromide, silver chloride and so forth.

In the light-sensitive materials of the invention, the silver halide grains of the silver halide emulsion layers thereof may be prepared in any of an acid process, a neutral process and an ammonia process. Such grains may be grown up at the same time or may be grown up after the seed grains thereof are grown up. The processes of preparing such seed grains and the processes of growing them up may be the same with or the different from each other.

In such a silver halide emulsion, silver halide ions and silver ions may be mixed up altogether at the same time, or either one out of the silver halide ions and the silver ions may be mixed up in a liquid containing the other ions.

Taking the critical growth rate of silver halide crystals into consideration, silver halide grains may be grown up by adding silver halide ions and silver ions at the same time but gradually into a mixing furnace while controlling the pH and pAg values in the furnace. According to the above-mentioned process, silver halide grains regular in crystal form and nearly uniform in grain size may be obtained. It is also allowed to change the halogen composition of such grains after the growth of the grains, in a conversion process.

In the course of preparing a silver halide emulsion, the sizes, configurations, distributions and growth rates each of the silver halide grains thereof may be controlled by making use of a silver halide solvent, if required.

The silver halide grains used in such silver halide emulsions are allowed to contain ions of a metal by making use of at least one kind selected from the group consisting of cadmium salts, zinc salts, lead salts, thallium salts, iridium salts, including the complex salts thereof, rhodium salts including the complex salts thereof and iron salts including the complex salts thereof in the course of forming and/or growing up the grains, so as to contain the metal element of the above-mentioned metal salts inside and/or on the surfaces of the grains. Also, the inside of the grains and/or the surfaces thereof may be endowed with reduction sensitization nuclei when the grains are placed in a suitably reducible atmosphere.

In such a silver halide emulsion, any unnecessary soluble salts may be removed therefrom after the growth of the silver halide grains completed or may remain in the grains as they are. The removal of such unnecessary salts may be carried out in accordance with the process described in, for example, Research Disclosure No. 17643.

The silver halide grains used in such silver halide emulsions may be either those having thereinside a uniform distribution of silver halide composition or those of the core/shell type having the different silver halide compositions between the inside of the grains and the surface layers thereof.

The silver halide grains used in such silver halide emulsions may be either those capable of forming latent images mainly on the grain surfaces or those forming latent images mainly inside the grains.

The silver halide grains used in such silver halide emulsions may be either those in the regular crystal forms such as cubic, octahedral, tetradecahedral and the like forms or those in such an irregular crystal form as a globular, tabular or the like form. To these grains, any ratio of a {100} plane to a {111} plane may be applied, and such grains may be either in the crystal complex forms or in various crystal forms mixed up together.

An average grain size of such silver halide grains, in which a grain size is defined as the diameter is defined as the diameter of a circle having an area equal to the projective area of a silver halide grain, is preferably not greater than 5 μm, more preferably, not greater than 3 μm.

As for such silver halide emulsions, it is not limitative to use those having any grain size distribution. That is, it is allowed to use either emulsions having a wide grain size distribution, which are called polydisperse emulsions, or emulsions having a narrow grain size distribution, which are called monodisperse emulsions. Such a monodisperse emulsion as expressed herein means an emulsion having a value not grreater than 0.20 that is obtained when the standard deviation value of a grain size distribution is divided by the value of an average grain size. A grain size expressed herein means a diameter of the grain in the case of a globular-shaped silver halide and a dimaeter of a circular image having the equivalent area to the area of the projective image of the grain in the case of any other shaped grains than the globular-shaped.

It is also allowed to use silver halide emulsions in the mixture of two or more kinds thereof which are separately prepared.

These silver halide emulsions may be chemically sensitized in ordinary processes such as a sulfur sensitizing process, a selenium sensitizing process, a reduction sensitizing process, a noble metal sensitizing process using gold or other noble metals, and so forth each of which may be applied independently or in combination.

Such silver halide emulsions may also be otpically sensitized to any desired wavelength region, by making use of the so-called spectral sensitizers which are well-known in photographic industry. Such spectral sensitizers may be used independently or in combination. Further, such silver halide emulsions are allowed to contain, as well as the above-mentioned spectral sensitizers, the so-called super color sensitizers which are comprised of the dyes incapable of functioning any spectral sensitization or the compounds substantially incapable of absorbing any visible rays of light, and which may be able to increase the sensitizing capacity of spectral sensitizers.

The spectral sensitizers used therein include, for example, a cyanine dye, a merocyanine dye, a conjugated cyanine dye, a conjugated merocyanine dye, a holopolar cyanine dye, a hemicyanine dye, a sterile dye and a hemioxanol dye.

The particularly useful dyes include, for example, a cyanine dye, a merocyanine dye and a conjugated merocyanine dye. Such dyes may be applied with any of the nuclei which are normally used in cyanine dyes so as to serve as basic heterocyclic nuclei. Such nuclei include, for example, the nuclei such as a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus and the nuclei each fused with an alicyclic hydrocarbon ring: and the above-mentioned nuclei each fused with an aromatic hydrocarbon ring, namely, an indolenine nucleus, a benzindolene nucleus, an indole nucleus, a benzoxazole nucleus, a naphthoxazole nucleus, aa benzothiazole nucleus, a naphthothiazole nucleus, a benzoselenazole nucleus, a benzimidazole nucleus, a quinoline nucleus and so forth. These nuclei may be substituted on a carbon atom.

To the merocyanine dyes and conjugated merocyanine dyes, it is allowed to apply a 5- or 6-membered heterocyclic nucle us to serve as a nucleus having a ketomethylene structure, such as a pyrazoline-5-one nucleus, a thiohydantoin nucleus, a 2-thiooxazolidine-2,4-dione nucleus, a thiazolidine-2,4-dione nucleus, a rhodanine nucleus, a thiobarbituric acid nucleus and so forth.

The useful spectral sensitizers include, for example, those described in Japanese Patent Examined Publication Nos. 14030/1969 and 24844/1977; West German Pat. No. 929,080; British Pat. No. 1,242,588; U.S. Pat. Nos. 2,231,658, 2,493,748, 2,503,776, 2,519,001, 2,912,329, 3,656,959, 3,672,897, 3,694,217, 4,025,349 and 4,046,572; and so forth.

These spectral sensitizers may be used independently or in combination. Such a combination of the spectral sensitizers are often used particularly for a super-color-sensitization. The typical cases thereof are given in, for example, Japanese Patent Examined Publication Nos. 4936/1968 and 12375/1978; Japanese Patent O.P.I. Publication Nos. 110618/1977 and 109925/1977; British Pat. Nos. 1,344,281 and 1,507,803; U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707.

The dyes incapable of displaying any spectral sensitizing function by themselves or the substances not substantially capable of absorbing any visible rays of light but capable of displaying a super color sensitizing function, each of which may be used together with the above-mentioned spectral sensitizers include, for example, such an aromatic organic acid formaldehyde condensation product as those described in U.S. Pat. No. 3,743,510, a cadmium salt, an azaindene compound, such an aminostyryl compound substituted by a nitrogen-containing heterocyclic group as those described in U.S. Pat. Nos. 2,933,390 and 3,635,721, and so forth. It is particularly advantageous to use the combination thereof described in U.S. Pat. Nos. 3,615,613, 3,615,641, 3,617,295 and 3,635,721.

It is alloawed to add the compounds which are well-known as an antifogging agent or a stabilizer in photographic industry into the above-mentioned silver halide emulsions, in the course of, at the time of and/or after a chemical sensitization, but before a silver halide emulsions are coated, with the purposes of preventing fogs or keeping photographic characteristics stable in the course of manufacturing, storing or photographically processing light-sensitive materials.

As for such antifogging agents and stablizers, the examples thereof may be given as follows:

Namely, azaindenes include, for example, pentazaindenes such as those described in U.S. Pat. Nos. 2,713,541, 2,743,180 and 2,743,181, tetrazaindenes such as those described in U.S. Pat. Nos. 2,716,062, 2,444,607, 2,444,605, 2,756,147, 2,835,581 and 2,852,375 and Research Disclosure No. 14851, triazaindenes such as those described in U.S. Pat. No. 2,772,164, polymerized azaindenes such as those described in Japanese Patent O.P.I. Publication No. 211142/1982, and so forth;

Quaternary onium salts include, for example, thiazolium salts such as those described in U.S. Pat. Nos. 2,131,038, 3,342,596 and 3,954,478, pyrylium salts such as those described in U.S. Pat. No. 3,148,067, phosphonium salts such as those described in Japanese Patent Examined Publication No. 40665/1975 and so forth;

Mercapto-substituted heterocyclic compounds include, for example, mercaptotetrazoles, mercaptotriazoles and mercaptodiazoles, such as those described in U.S. Pat. Nos. 2,403,927, 3,266,897 and 3,708,303, and Japanese Patent O.P.I. Publication Nos. 135835/1980 and 71047/1984, a mercaptodiazole such as those described in U.S. Pat. No. 2,824,001, a mercaptobenzthiazole and a mercaptobenzimidazole, such as those described in U.S. Pat. No. 3,397,987, a mercaptooxadiazole such as those described in U.S. Pat. No. 2,843,491, a mercaptothiadiazole such as those described in U.S. Pat. No. 3,364,028, and so forth;

Polyhydroxybenzenes including, for example, a catechol such as those described in U.S. Pat. No. 3,236,652 and Japanese Patent Examined Publication No. 10256/1968, a resorcine such as those described in Japanese Patent Examined Publication No. 44413/1981, a gallate such as those described in Japanese Patent Examined Publication No. 4133/1968, and so forth;

Azoles including, for example, a tetrazole such as those described in West German Pat. No. 1,189,380, a triazole such as those described in U.S. Pat. No. 3,157,509, a benzotriazole such as those described in U.S. Pat. No. 2,704,721, an urazol such as those described in U.S. Pat. No. 3,287,135, a pyrazole such as those described in U.S. Pat. No. 3,106,467, an indazole such as described in U.S. Pat. No. 2,271,229, a polymerized benzotriazole such as those described in Japanese Patent O.P.I. Publication No. 90844/1984, and so forth;

Heterocyclic compounds including, for example, a pyrimidine such as those described in U.S. Pat. No. 3,161,515, a 3-pyrazolidone such as those described in U.S. Pat. No. 2,751,297, a polymerized pyrolidone, i.e., a polyvinyl pyrolidone such as those described in U.S. Pat. No. 3,021,213, and so forth;

Various kinds of inhibitor precursors such as those described in Japanese Patent O.P.I. Publication Nos. 130929/1979, 137945/1984 and 140445/1984, British Pat. No. 1,356,124, U.S. Pat. Nos. 3,575,699 and 3,649,267, and so forth;

Sulfinic acid and the sulfinic acid derivatives such as those described in U.S. Pat. No. 3,047,393;

Inorganic salts such as those described in U.S. Pat. Nos. 2,556,263, 2,839,405 and 2,488,709, 2,728,663; and so forth.

As for the binders (or the protective colloids) to be used in the silver halide emulsions of the light-sensitive materials of the invention, a gelatin may be advantageously used for. It is also allowed to use therein hydrophilic colloids including, for example, a gelatin derivative, a graftpolymer of gelatin and other high molecules, and a protein, a sugar derivative, a cellulose derivative or a synthetic hydrophilic high molecular substances such as a mono- or co-polymer, other than the above.

As for the gelatins, besides a lime-treated gelatin, an acid-treated gelatin and such an oxygen-trreated gelatin as described in Bulletin of Society of Photographic Science and Technology of Japan, No: 16, page 30, (1966) may be used and, in addition, the hydrolyzed or enzyme-decomposed matters of gelatin may also be used. As for the gelatin derivatives which may be used therein, they include, for example, those obtained by the reaction of gelatin with a variety of compounds such as an acid halide, an anhydrous acid, an isocyanate, a bromoacetic acid, an alkanesul tone, a vinyl sulfonamide, a maleinimide compound, a polyalkylene oxide, an epoxy compound and so forth. The typical examples thereof are described in U.S. Pat. Nos. 2,614,928, 3,132,945, 3,186,846 and 3,312,553, British Pat. Nos. 861,414, 1,033,189 and 1,005,784, Japanese Patent Examined Publication No. 26845/1967, and so forth.

The preferable proteins include, for example, albumin and casein, the preferable cellulose derivatives include, for example, a hydroxyethyl cellulose, a carboxymethyl cellulose and a cellulose sulfate, and the preferable sugar derivatives include, for example, a sodium alginate and a starch derivative.

The above-mentioned graft polymers of gelatin and other high molecules to be used therein include, for example, those grafting gelatin into the mono- (homo-) or co-polumer of vinyl monomers such as acrylic acid and the esters thereof, methacrylic acid and the esters thereof, the derivatives of amide or the like, acrylonitrile, styrene and so forth. It is particularly preferable to use the graft polymers of the polymers compatible in some extent with gelatin, such as those of acrylic acid, acrylamide, methacrylamide, hydroxyalkyl methacrylate and so forth. The examples thereof are described in U.S. Pat. Nos. 2,763,625, 2,831,767 and 2,956,884, and so forth.

The typical synthetic hydrophilic high molecular substances include, for example, homo- or co-polymers of polyvinyl alcohol, partially acetalized polyvinyl alcohol, poly-N-vinyl pyrolidone, polyacrylic acid, polymethacrylic acid, polyacrylamide, polyvinyl imidazole, polyvinyl pyrazole and so forth. They are described in, for example, West German Patent (OLS) No. 2,312,708, U.S. Pat. Nos. 3,620,751 and 3,879,205, and Japanese Patent Examined Publication No. 7561/1968.

The photographic emulsion layers and the other hydrophilic colloidal layers of the light-sensitive materials of the invention may be hardened by making use of two or more kinds of hardeners capable of cross-linking the molecules of binders or protective colloids and increasing a layer hardness. Such hardeners may be added to a light-sensitive material, in such an amount as is capable of hardening the light-sensitive material without further adding any hardener into processing liquids. However, such hardeners may also be added into a processing liquid.

As for the hardeners to be used therein, they include, for example, the aldehyde type and aziridine type hardeners such as those described in PG Report No. 19,921, U.S. Pat. Nos. 2,950,197, 2,964,404, 2,983,611 and 3,271,175, Japanese Patent O.P.I. Publication No. 40898/1971 and Japanese Patent O.P.I. Publication No. 91315/1975, the isoxazole type hardeners such as those described in U.S. Pat. No. 331,609, the epoxy type hardeners such as those described in U.S. Pat. No. 3,047,394, West German Pat. No. 1,085,663, British Pat. No. 1,033,518, and Japanese Patent Examined Publication No. 35495/1973, the vinyl sulfon type hardeners such as those described in PB Report No. 19,020, West German Pat. Nos. 1,100,942, 2,337,412, 2,545,722, 2,635,518, 2,742,308 and 2,749,260, British Pat. No. 1,251,091, Japanese Patent Application Nos. 54236/1970 and 110996/1973, and U.S. Pat. Nos. 3,539,644 and 3,490,911, the acryloyl type hardeners such as those described in Japanese Patent Application No. 27949/1973, and U.S. Pat. No. 3,640,720, the carbodiimide type hardeners such as those described in U.S. Pat. Nos. 2,938,892, 4,043,818 and 4,061,499, Japanese Patent Examined Publication No. 38715/1971, and Japanese Patent Application No. 15095/1974, the triazine type hardeners such as those described in West German Pat. Nos. 2,410,973 and 2,553,915, U.S. Pat. No. 3,325,287, and Japanese Patent O.P.I. Publication No. 12722/1977, the high molecule type hardeners such as those described in British Pat. No. 822,061, U.S. Pat. Nos. 3,623,878, 3,396,029 and 3,226,234, and Japanese Patent Examined Publication Nos. 18578/1972, 18579/1972 and 48896/1972, and, besides the above, the hardeners of the maleimide type, acetylene type, methanesulfonate type and the N-methylol type may be used independently or in combination. The useful technologies for such combination use are given in, for example, West German Pat. Nos. 2,447,587, 2,505,746 and 2,514,245, U.S. Pat. Nos. 4,047,957, 3,832,181 and 3,840,370, Japanese Patent O.P.I. Publication Nos. 43319/1973, 63062/1975 and 127329/1977, and Japanese Patent Examined Publication No. 32364/1973.

The photographic emulsion layers and other hydrophilic colloidal layers of the light-sensitive materials of the invention are allowed to contain the dispersion, i.e., the latex, of a water-insoluble or hardly soluble synthetic polymer, with the purposes of improving the dimensional stability and so forth of the light-sensitive material.

The hardly soluble synthetic polymers are preferably include, for example, those described in British Pat. Nos. 807,894 and 1,186,699; Japanese Patent Examined Publication No. 43125/1973, 25499/1974; U.S. Pat. Nos. 2,376,005, 2,853,457, 2,956,884, 3,062,674, 3,287,289, 3,411,911, 3,488,708, 3,525,620, 3,607,290, 3,635,715 and 3,645,740; and so forth.

This invention can be applied to multicolor photographic light-sensitive materials each provided on the support thereof with multilayers having at least two different spectral sensitivities. Ordinarily, these multilayered multicolor photographic light-sensitive materials are provided on the support thereof with at least one each of red-sensitive, green-sensitive and blue-sensitive emulsion layers, and any of the layer arrangements may be freely selected so as to meet the requirements. In the ordinary cases, the red-sensitive layer contain cyan couplers, the green-sensitive layers contain magenta couplers, and the blue-sensitive layers contain yellow forming couplers.

Such light-sensitive materials of the invention may be exposed to light by making use of magnetic waves having a spectral wavelength region to which the emulsion layers thereof each sensitive. The light light-sources useful therein include, for example, any of the well-known ones such as natural light, i.e., daylight, a tungsten lamp, a fluorescent lamp, a mercury lamp, a Xenon-arc lamp, a carbon-arc lamp, a Xenon-flash lamp, a cathode-ray-tube flying spot, a variety of laser beams, a light-emitting diode, such a phosphor as is excited by electron rays, x-rays, $\gamma$-rays, $\alpha$-rays and so forth.

Such exposures may be made not only for a time from 1 millisecond to 1 second for which ordinary type cameras apply, but also for 1 microsecond or shorter such as a time from 100 nanoseconds to 1 microsecond with the use of a CRT or a Xenon-flash, for example, as well as for a time not shorter than 1 second. These exposure may also be made either continuously or intermittently.

The light-sensitive materials of the invention may be processed in any of the well-known color developing processes. Color images may also be reproduced in a reversal process. When a color image is to be reproduced in such a reversal process, the light-sensitive materials of the invention are to be treated in a black-and-white developing step, then applied to a white exposure without any fixing step or then treated in a bath containing a fogging agent and, further, treated in a color developing step. The step for applying a white exposure or the step for treating with a fogging agent may be the same as a color developing step.

Each of the processing steps is ordinarily carried out by soaking light-sensitive materials in processing liquids. However, it is also allowed to process the light-sensitive materials in the other processes including, for example, a spray-processing system in which a processing liquid is supplied in the spray-form, a web-processing system in which a light-sensitive material is brought into contact with a carrier member impregnated with a processing liquid, a system in which a viscous-development is carried out, and so forth.

A color development process is comprised of a color developing step, a bleaching step, a fixing step, a washing step and, if required, a stabilizing step. It is also allowed to apply a bleach-fixing step with the use of a monobath type bleach-fixer in place of both steps of using a bleaching agent and of using a fixer and, further, to apply a monobath processing step in which each of a color development, a bleaching treatment and a fixing treatment can be performed in only one bath with the use of a monobath type developing, bleaching and fixing liquid.

It is allowed to combine therewith a prehardening step, the neutralizing step therefor, a stopping and fixing step, a posthardening step and so forth. In these steps, it is also allowed to take an activator-processing step, in place of the color developing step, in which a color developing agnet or the precursor thereof is contained in advance in a light-sensitive material and the development thereof is made by an activator, and it is further allowed to take such an activator-processing step, a bleaching step and a fixing step may be carried out at the same time, in place of a monobath type processing step. In these processing steps, either one of a washing step or a combination step of washing and stabilizing is to be carried out as the final step thereof.

Color developing step→Bleaching step→Fixing step;
Color developing step→Bleach-fixing step;
Prehardening step→Color developing step→Stopping-fixing step→Washing step→Bleaching step→Fixing step→Washing step→Posthardening step;
Color developing step→Washing step→Auxiliary color developing step→Stopping step→Bleaching step→Fixing step;
Monobath processing step;
Activator processing step→Bleach-Fixing step;
Activator processing step→Bleaching step→Fixing step.

Any of the well-known processing liquids may be applied to the light-sensitive materials of the invention. The temperatures for processing the light-sensitive materials may be selected ordinarily from 18° C. to 50° C. and it is, however, allowed to set the temperature lower than 18° C. or higher than 50° C.

Normally, color developers are comprised of an aqueous alkaline solution containing a color developing agent. Such color developing agents as are to be used therein include, for example, the well-known and prevailing aromatic amine developing agents such as a phenylenediamine e.g., 4-amino-N,N-diethylaniline, 3-methyl-4-amino-N,N-diethylaniline, 4-amino-N-ethyl-N-$\beta$-hydroxyethylaniline, 3-methyl-4-amino-N-ethyl-N-$\beta$-hydroxyethylaniline, 3-methyl-4-amino-N-ethyl-N-$\beta$-methanesulfonamidoethylaniline, 4-amino-3-methyl-N-ethyl-N-$\beta$-methoxyethylaniline and so forth).

Besides the above, it is also allowed to use those described in, for example, L. F. A. Mason, 'Photographic Processing Chemistry' (Focal Press, 1966), pp. 226–229; U.S. Pat. Nos. 2,193,015 and 2,592,364; Japanese Patent O.P.I. Publication No. 64933/1973; and so forth.

The color developers are also allowed to contain such a pH buffers as the sulfites, carbonates, borates, phosphates and the like of an alkali metal, such a development inhibitor or antifogging agent as a bromide, iodide and an organic antifogging agent, and so forth. If required, it is also allowed to contain a water softener, a preserving agent such as hydroxylamine, an organic solvent such as benzyl alcohol and diethylene glycol, a development accelerator such as a polyethylene glycol, a quaternary ammonium salt or an amine, a dye-forming coupler, a competing coupler, a fogging agent such as sodium borohidride, an auxiliary developer such as 1-phenyl-3-pyrazolidone, a thickening agent, a polycarboxylic acid type chelating agent such as those described in U.S. Pat. No. 4,083,723, an oxidation inhibitor such as those described in West German Patent (OLS) No. 2,622,950, and so forth.

A photographic emulsion layer is normally bleached after it was color-developed. Such bleaching treatment and a fixing treatment may be made either at the same time or separately. Such bleaching agents used therein include, for example, polyvalent metal compounds such as those of iron (III), cobalt (III), chromium (VI), chromium (II) and so forth, a peroxy acids, quinones, nitro compounds and so forth. A ferricyanide, a dichromate, an organic complex salt of iron (III) or cobalt (III) may be given as the examples thereof and they include such an aminopolycarboxylic acid as ethylenediamine tetraacetic acid, nitrilotriacetic acid, 1,3-diamino-2-propanoltriacetic acid and so forth, or the complex salts of such an organic acid as citric acid, tartaric acid, malic acid and so forth; a persulfate and a permanganate; nitrosophenol; and so forth. Among these bleaching agents given above, potassium ferricyanate, iron (III) sodium ethylenediaminetetraacetate and iron (III) ammonium ethylenediaminetetraacetate are particularly useful. Such iron (III) ethylenediaminetetraacetate complex salts are useful not only in the case of an independent bleaching liquid but also in the case of a monobath type bleaching and fixing liquid.

Such bleaching liquids or bleaching-fixing liquids are also allowed to contain not only such a bleaching accelerator as those described in U.S. Pat. Nos. 3,042,520 and 3,241,966, Japanese Patent Examined Publication Nos. 8506/1970 and 8836/1970 and so forth, and thiol compounds such as those described in Japanese Patent O.P.I. Publication No. 65732/1978, bt also a variety of additives.

The silver halide photographic light-sensitive materials of the invention contain a novel cyan coupler. Therefore, the spectral absorption characteristics of the cyan dyes formed therein are excellent. Namely, the spectral absorption is sharp-cut on the short wavelength side and the irregular absorption is substantially less in the green and bluespectral regions and also the color reproductibility of the cyan dyes is excellent. In addition, the spectral absorption coefficient of the cyan dyes is substantially great and, therefore, the sharpness can be improved by a thinner coating or the like techniques.

EXAMPLES

The invention will now be described with reference to the following examples and it is, however, to be understood that the invention shall not be limited thereto.

EXAMPLE-1

The following comparative coupler (A) was dissolved with heating together with one half by weight as much dibutyl phthalate and three times by weight as much ethyl acetate, as the comparative coupler (A). The resulted solution was so dispersed as to be emulsified in a 5% gelatin solution by making use of Alkanol XC manufactured by DuPont serving as an activator. The resulted dispersion was added to and mixed with a silver chlorobromide emulsion having a silver bromide content of 80 mol% to as to contain the couplers in a proportion of 0.35 mol per mol of the silver contained. The resulted matter was coated over to a paper support laminated on the both sides with polyethylene and dried up, so that Sample-1 was obtained. The amount of the coupler coated was $1.2 \text{ g} \times 10^{-5}$ mol/100 cm$^2$, the amount of silver coated was 3.7 mg/100 cm$^2$ and the amount of gelatin coated was 16 mg/100 cm$^2$.

Next, Samples No. 2 through No. 8 were obtained in the same manner as in Sample-1, except that the coupler used in Sample-1 was replaced by the couplers each indicated in Table-1, provided, however, that the amount of silver coated was doubled as far as 4-equivalent couplers were concerned.

These samples were exposed to light through an optical wedge and were then treated in the following steps in accordance with an ordinary processing method.

|  | Processing temperature | Processing time |
|---|---|---|
| Color developing | 33° C. | 3 min. 30 sec. |
| Bleach-fixing | 33° C. | 1 min. 30sec. |
| Washing | 33° C. | 3 min. |
| Drying | 50 to 80° C. | 2 min |

The composition of each processing liquid is as follows:

| [Color developer] | |
|---|---|
| Benzyl alcohol | 12 ml |
| Diethylene glycol | 10 ml |
| Potassium carbonate | 25 g |
| Sodium bromide | 0.6 g |
| Sodium sulfite, anhydrous | 2.0 g |
| Hydroxylamine sulfate | 2.5 g |
| N—ethyl-N—β-methanesulfonamidethyl-3-methyl-4-aminoaniline sulfate | 4.5 g |
| Water to be added to make | 1 liter |
| pH value to be adjusted with NaOH to | pH 11 |
| [Bleach-fixer] | |
| Ammonium thiosulfate | 120 g |
| Sodium metahydrogensulfite | 15 g |
| Sodium sulfite, anhydrous | 3 g |
| Ferric ammonium EDTA | 65 g |
| Water to be added to make | 1 liter |
| pH value to be adjusted to | pH 6.7 to 6.8 |

The sensitometric measurements of the processed Samples No. 1 through No. 10 were made by means of a densitometer, Model KD-7R manufactured by Konishiroku Photo Ind. Co., Ltd. The Dmax values of the samples are relative to that of Sample No. 1 which is regarded as 100 and the Dwax values were measured through transmitted light.

With respect to the dye images reproduced on every processed sample, each of the reflection spectra at a λmax of 1.0 was measured by a Hitachi's automatic recording spectro-photometer model 320 attached with an integrating sphere. Magnesium oxide was used on the reference side.

The degrees of the spectral absorptions on the short wavelength side were obtained according to the following definition.

Δλs=λmax—(a wavelength making reflection density to be 0.2)

The less a value of Δλs is, the more an spectral absorption is sharper.

The results of the measurements are shown in Table-1.

TABLE 1

| Sample No. | Coupler | Relative Dmax | λmax | Δλs | Remark |
|---|---|---|---|---|---|
| 1 | Comparative (A) | 100 | 654 | 145 | Comparative sample |
| 2 | Comparative (B) | 89 | 643 | 149 | Comparative sample |
| 3 | Exemplified (2) | 125 | 651 | 120 | Invention sample |
| 4 | Exemplified (17) | 123 | 632 | 122 | Invention sample |
| 5 | Exemplified (18) | 120 | 631 | 120 | Invention sample |
| 6 | Exemplified (6) | 130 | 636 | 123 | Invention sample |
| 7 | Exemplified (15) | 135 | 663 | 120 | Invention sample |
| 8 | Exemplified (16) | 128 | 658 | 115 | Invention sample |
| 9 | Exemplified (28) | 110 | 641 | 130 | Invention sample |
| 10 | Exemplified (29) | 115 | 654 | 125 | Invention sample |

Each absorbance of the dyes formed upon oxidation coupling reaction of each coupler with the above-mentioned color developing agent was measured by making use of ethyl acetate to serve as the solvent. The results thereof are shown in Table-2.

TABLE-2

| Sample No. | Coupler | Mol absorption coefficient |
|---|---|---|
| 11 | Comparative coupler (A) | $2.34 \times 10^4$ |
| 12 | Comparative coupler (C) | $1.75 \times 10^4$ |
| 13 | Exemplified coupler (2) | $6.46 \times 10^4$ |
| 14 | Exemplified coupler (17) | $5.76 \times 10^4$ |
| 15 | Exemplified coupler (18) | $4.37 \times 10^4$ |
| 16 | Exemplified coupler (6) | $5.57 \times 10^4$ |
| 17 | Exemplified coupler (15) | $6.20 \times 10^4$ |
| 18 | Exemplified coupler (16) | $7.31 \times 10^4$ |
| 19 | Exemplified coupler (31) | $4.38 \times 10^4$ |
| 20 | Exemplified coupler (32) | $4.67 \times 10^4$ |

Comparative Coupler (A)

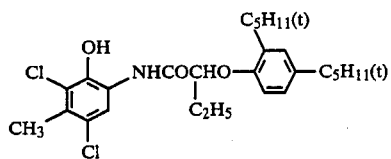

Comparative Coupler (B)

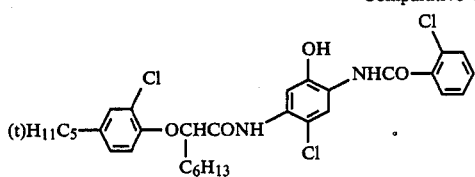

Comparative Coupler (C)

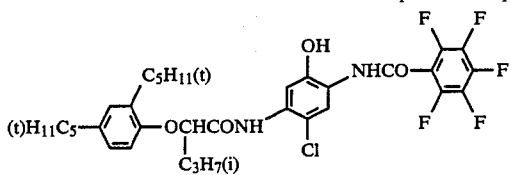

FIG. 1 exhibits the spectral reflection density curves No. 1 of Sample No. 1 and No. 2 of Sample No. 3 respectively.

As are obvious from Table-1 and FIG. 1, it can be found that the cyan couplers of the invention display substantially sharp-cut spectral absorption characteristics and excellently less spectral absorption in both green and blue spectral regions, as compared with the comparative couplers. In particular, each of Samples 3, 7, 8, 9 and 10 containing the couplers represented by Formula [II] has a λmax relatively closer to the long wavelength side and displays the color tones suitable for serving as cyan couplers.

It can also be found from Table-2 that the dyes formed of the cyan couplers of the invention have a very high absorption coefficient, as compared with the comparative couplers, and each of Samples 13, 17 and 18 containing the couplers represented by Formula [II] has a particularly high absorption coefficient.

EXAMPLE-2

A sample of silver halide color photographic light-sensitive material (Sample No. 21) was prepared in such a manner that each of the following layers was coated over to a paper support laminated on the both sides thereof with polyethylene in order from the support side.

The 1st layer

A layer containing 1.2 g/m² of gelatin, 0.32 g/m² of a blue-sensitive silver chlorobromide emulsion in terms of silver and so forth on and having a silver chloride content of 98 mol%, and 0.50 g/m² of dioctyl phthalate in which 0.80 g/m² of yellow couplers, Y-1, were dissolved.

The 2nd layer

An interlayer containing 0.70 g/m² of gelatin, 8 mg/m² of an antiirradiation dyestuff, AI-1, and 4 mg/m² of another antiirradiation dyestuff, AI-2.

The 3rd layer

A layer containing 1.25 g/m² of gelatin, 0.20 g/m² of a green-sensitive silver chlorobromide emulsion having a silver chloride content of 97 mol% and 0.30 g/m² of dioctyl phthalate in which 0.62 g/m² of magenta couplers, M-1, were dissolved.

The 4th layer

An interlayer containing 1.20 g/m² of gelatin.

The 5th layer

A layer containing 1.20 g/m², 0.30 g/m² of a red-sensitive silver chlorobromide emulsion having a silver chloride content of 96 mol% and 0.20 g/m² of dioctyl phthalate in which 0.45 g/m² of cyan coupler A were dissolved.

The 6th layer

A layer containing 1.00 g/m² of gelatin and 0.20 g/m² of dioctyl phthalate in which 0.30 g/m² of a UV absorbing agent, UV-1, were dissolved.

The 7th layer

A layer containing 0.50 g/m² of gelatin.

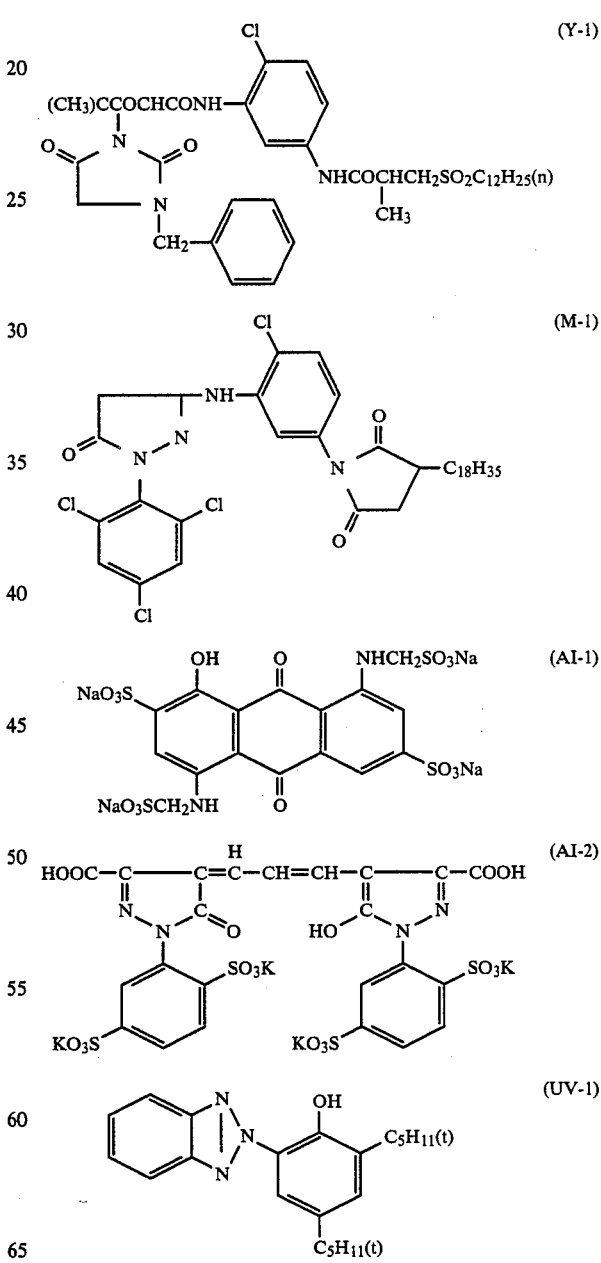

Further, the above-mentioned 2nd, 4th and 7th layers each were added with sodium 2,4-dichloro-6-hydroxy- S-triazine to serve as a hardening agent in an amount of 0.017 g per gram of gelatins used in each of the layers.

In the meantime, Sample No. 22 was also prepared in the same manner as in Sample No. 21, except that Cyan Coupler A used in Sample No. 21 was replaced by Exemplified Coupler 2.

Next, a Macbeth chart was photographed with a roll of SAKURA Color SR 100 film to obtain a negative image and the image was printed on the above-mentioned light-sensitive material samples No. 21 and No. 22, respectively, and the samples were processed in the same method as was taken in Example-1. The results were compared visually with each other.

It was found that Sample No. 22 was improved in blue and cyan color-separation, in color reproducibility and also in luminosity in green, as compared with Sample No. 21. As is obvious from FIG. 1, it is found that the above-mentioned effects are derived from the dyes which are so formed of the cyan couplers of the invention as to display an excellent spectral absorption that is substantially less in green and blue spectral regions.

What is claimed is:

1. A silver halide color photographic light-sensitive material comprising a support having thereon at least one silver halide emulsion layer containing a cyan dye-forming coupler represented by the following Formula II:

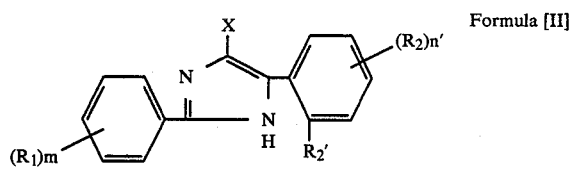

Formula [II]

wherein $R_1$ and $R_2$ each represent a group capable of being a substituent of a phenyl group, $R_2'$ is selected from the group consisting of —NHCOR$_3$,

—NHCOOR$_3$, —NHSO$_2$R$_3$,

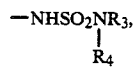

—NHR$_3$, and hydroxy; $R_3$ and $R_4$ each represent a hydrogen atom, an alkyl group or an aryl group; m is an integer from 0 to 5, and n' is an integer from 0 to 4, provided that $R_1$ and $R_2$ may be the same or different when the total of m and n' is not less than 2; and X represents a group or an atom capable of being split off from the coupler upon reaction of an oxidized product of a color developing agent with the coupler residue; and the total number of carbon atoms contained in the groups represented by $R_1$, $R_2$, $R_2'$ and X is from 8 to 50.

2. The silver halide photographic light-sensitive material of claim 1, wherein said cyan dye forming coupler is contained in said silver halide emulsion layer in an amount of from 0.07 to 0.7 mol per mol of silver contained in said silver halide emulsion layer.

3. The silver halide photographic light-sensitive material of claim 2, wherein said cyan dye forming coupler is contained in said silver halide emulsion layer in an amount of from 0.1 to 0.4 mol per mol of silver contained in said silver halide emulsion layer.

* * * * *